United States Patent [19]

Grier et al.

[11] 4,049,559
[45] Sept. 20, 1977

[54] COMPOSITION FOR SECONDARY AND TERTIARY OIL RECOVERY

[75] Inventors: Nathaniel Grier, Englewood, N.J.; Richard A. Dybas, Center Square, Pa.; Robert A. Strelitz, Edison, N.J.

[73] Assignee: Merck & Co., Inc., Rahway, N.J.

[21] Appl. No.: 687,580

[22] Filed: May 18, 1976

Related U.S. Application Data

[63] Continuation-in-part of Ser. No. 620,721, Oct. 9, 1975, abandoned, which is a continuation-in-part of Ser. No. 540,620, Jan. 13, 1975, abandoned.

[51] Int. Cl.² ............ E21B 43/22; A01N 9/20; A61L 13/00
[52] U.S. Cl. .............. 252/8.55 D; 166/273; 166/274; 252/390; 424/325
[58] Field of Search ............ 252/8.55 D; 166/273, 166/274, 275; 424/325

[56] References Cited

U.S. PATENT DOCUMENTS

| | | | |
|---|---|---|---|
| 2,867,299 | 1/1959 | Cocks | 252/8.55 |
| 3,049,492 | 8/1962 | DeGroote et al. | 252/8.55 |
| 3,197,510 | 7/1965 | Cyba | 260/584 |
| 3,467,705 | 9/1969 | Gigante et al. | 260/558 |
| 3,483,254 | 12/1969 | Shen et al. | 260/563 |
| 3,885,626 | 5/1975 | Gale et al. | 166/273 |
| 3,900,565 | 8/1975 | Grisar et al. | 424/274 |

FOREIGN PATENT DOCUMENTS

| | | |
|---|---|---|
| 860,860 | 2/1961 | United Kingdom |
| 1,305,502 | 2/1973 | United Kingdom |

*Primary Examiner*—Herbert B. Guynn
*Attorney, Agent, or Firm*—Edmunde D. Riedl; Julian S. Levitt

[57] ABSTRACT

An antimicrobial composition for secondary and tertiary oil recovery comprising a flooding composition consisting of displacement and driving fluids having incorporated therein an antimicrobially effective amount of a di-bicyclo[3.1.1] or [2.2.1] heptyl or di-bicyclo[3.1.1] and [2.2.1] heptenyl polyamines or salts thereof.

4 Claims, No Drawings

COMPOSITION FOR SECONDARY AND TERTIARY OIL RECOVERY

DISCLOSURE OF THE INVENTION

This application is a continuation-in-part of U.S. Ser. No. 620,721 filed Oct. 9, 1975 which is a continuation-in-part of U.S. Ser. No. 540,620 filed Jan. 13, 1975, both now abandoned. U.S. Ser. No. 620,721 filed Oct. 9, 1975 is specifically incorporated herein by reference.

This invention relates to an improved flooding composition and process for secondary and tertiary oil recovery comprising water and oil soluble antimicrobials in combination with displacement and driving fluids.

Recovery of oil by flooding with a displacement fluid is a well known technique for revitalizing developed oil fields. Previously, as primary recovery techniques exhausted a field, newer fields exploitable by primary recovery were preferentially developed. Lately as exploration to develop newer fields has become more risky and costly, and as the price of crude petroleum becomes more attractive, enhanced oil recovery techniques are becoming ever more widely practiced in the petroleum industry. It is estimated that 25 to 60 billion barrels of oil are recoverable from U.S. fields with these methods.

Secondary oil recovery techniques are well known and are a common practice. Following secondary recovery, tertiary recovery may be employed by adding to waters and brines such chemicals as surfactants, e.g., hydrocarbon sulfates and sulfonates, co-surfactants such as alkanols and alkanol ethers, thickeners and viscosity modifiers (mobility control agents), corrosion inhibitors, emulsifiers, and the like to form a microemulsion with displaced oil. This in turn is brought to the surface with additional volumes of displacement and driving fluids. This tertiary recovery technique is described in detail in U.S. Pat. No. 3,885,626.

In the usual secondary or tertiary recovery process, displacement and driving fluids are injected into a subterranean formation through a plurality of injection wells which surround one or more producing wells. The displacement and driving fluids are forced through the injection well bores into the formation. There these fluids act to remove the oil and push it toward the producing well where it is recovered by conventional methods. Most commonly, water or brine comprises the injection fluid in secondary oil recovery.

The almost universal practice is to include viscosity modifying agents in the injection fluid to increase its viscosity. Suitable agents for modifying viscosity are well known water soluble polymers and include the natural and synthetic gums, e.g., guar gums, xanthan gums, and the like as well as cellulosic derivatives such as carboxyalkyl cellulose, hydroxyalkyl cellulose and the like. Also included as suitable viscosity modifying agents are the modified starches and starch derivatives and polymers of the polyacrylamide type. Such viscosity increasing agents and techniques for their use are amply disclosed in the literature, for example, U.S. Pat. No. 2,731,414 where Binder et al disclose the use of carboxymethyl cellulose, locust bean gum, gum Karaya, and Irish moss for increasing the viscosity of the injection fluid. In U.S. Pat. No. 2,771,138, Beeson discloses the use of a combination of sugar and a metal salt. Sparks in U.S. Pat. No. 3,053,765 teaches the incorporation of a polysaccharide to thicken the injection fluid while Lindblom et al, U.S. Pat. No. 3,305,016, teach the use of a heteropolysaccharide made by a bacterium of the genus Xanthomonas.

In addition to such naturally occurring compounds, synthetic polymers are employed as in U.S. Pat. No. 2,842,492; von Engelhardt et al. teach the use of copolymers of methacrylic acid and methyl methacrylate as thickening agents. Zerweck et al in U.S. Pat. No. 3,020,953, Sandiford et al, in U.S. Pat. No. 2,827,964 and McKennon, U.S. Pat. No. 3,039,529 teach the use of water soluble polyacrylamides. See also Sandiford et al, U.S. Pat. No. 3,116,791, where the use of water soluble polyalkylene oxides is taught. Kaufman in Canadian Pat. No. 864,433 proposes the use of N-sulfohydrocarbon substituted acrylamides. Cross-linked polyacrylamide is used in certain types of well treatment in Holbert et al, U.S. Pat. No. 3,210,310.

The technique of "selective plugging" of more permeable sections of the formation in order to increase flow in a less permeable section, through the use of various synthetic water soluble polymers is disclosed by Bond et al., U.S. Pat. No. 2,864,448.

One widely used synthetic polymer is partially hydrolyzed polyacrylamide. For example, see Cooper, U.S. Pat. No. 3,418,239.

Synthetic polymers such as acrylamide polymers are used in oil recovery together with ammonium hydroxide (U.S. Pat. No. 3,367,418) and with polyvalent cations (U.S. Pat. No. 2,842,338); cationic polymers may be employed because of their advantages as outlined in U.S. Pat. No. 3,744,566. Generally, any polymeric material is satisfactory so long as it adequately adjusts the viscosity, remains in solution in the driving and displacement fluids, resists elevated temperatures and mechanical shear forces.

Varied bacteria cause serious problems in water flooding operations for oil recovery. They include sulfate-reducers, iron bacteria, capsule or slime-formers and others. Algae and particular fungi are also implicated in various surface components of the total recovery systems. Oil sands may become impervious to the injection fluids because of insoluble metal sulfides formed from metal ions and microbial reduction of sulfate, or in the presence of gelatinous slimes produced by microbial oxidation of iron to ferric hydroxide and other conversions. Unfortunately, the injection fluid itself may serve as the inoculum and nutrients for these bacteria. This serious problem has hampered the full potential of the application of secondary and tertiary recovery. When such bacteria proliferate in oil fields, the sulfuric and sulfurous acids produced thereby also have an extremely deleterious effect on metallic equipment subject to the corrosive attack of such acids. The use of antibacterials to inhibit the growth of such bacteria has thus far not been entirely satisfactory because of poor efficiencies, narrow antimicrobial spectrum, unsatisfactory partitioning between oil and water phases, chemical or thermal instability and the like.

We have now found that the inclusion of any of the novel compounds set forth in U.S. Ser. No. 620,721 filed Oct. 9, 1976 and especially 1-[1,5-di-(3,3-dimethylnorborn-2-yl)-3-pentyl]-1,5,9-triazanonane or its salts is surprisingly effective in inhibiting the growth of sulfate reducing bacteria and other types, as well as providing protection to surfaces subject to corrosion, e.g., metallic surfaces exposed to brine.

In carrying out the invention, solutions or dispersions of the antimicrobial are preferably prepared by admixing with water, brine, and/or organic solvents and addition to flooding fluids may be made by continuous metering to the flow or in portions. Alternatively, the viscosity modifying agent may be first dissolved in water or brine, followed by the addition of the antimicrobial agent, or an aqueous solution or dispersion of antimicrobial and viscosity modifying agent may be diluted with brine to form a solution having ionic constituents similar or identical to those in the water in the oil field wherein the recovery procedure is to be employed.

In a preferred method of operation, a flooding composition is prepared with oil field brine obtained from the producing strata or from strata adjacent to the producing strata whereby undesired changes in the strata by reason of introduction of the pusher fluid are minimized and the antimicrobial admixed with this fluid. The prior art describes in detail the preparation of displacement and driving fluids to which the antimicrobial described herein is then incorporated. The concentrations are calculated and adjusted so that the antimicrobial is present in the finished flooding composition at a concentration of 0.1 to 400 ppm, (0.00001 to 0.04% by weight).

In recovery operations, the concentration of the viscosity modifying agent in the injected fluid is adjusted to produce the desired viscosity. In general, with high molecular weight viscosity modifying agents, it is desirable to use from about 0.01 to 0.5 percent by weight or more of such agent in the fluid. In practice, the fluid may have a viscosity of from slightly over that of pure water (1.0 centipoise at 20° C.) to about 1,000 centipoises and preferably from about 1.1 to 100 centipoises. The exact viscosity to be employed for maximum efficiency in recovery of oil will vary depending upon such factors as the porosity and permeability of the oil-bearing formation, the viscosity of the oil in the formation and the particular type of oil-bearing strata involved. In many cases, good results are obtained when the fluid is adjusted to a viscosity ranging from about the viscosity of the oil in place in the producing strata to about one-half the viscosity of such oil or even above the oil viscosity.

The antimicrobial can be employed as an acid addition salt, e.g., the hydrochloride to increase its solubility in an aqueous injection fluid. If used as the base compound, the antimicrobial is usually not completely soluble, but so long as it is uniformly admixed or emulsified with the injection fluid its activity is not seriously affected. However, when so used as the base compound, the polyamine is preferably dissolved in a solvent in combination with a solvent soluble surfactant. Suitable solvents include aliphatic and aromatic hydrocarbons that are fluid at ambient temperature including petroleum fractions such as kerosene; xylene; toluene; mineral spirits and the like. Gasoline and similar hydrocarbons are suitable solvents, but their low flash point presents hazards that while not precluding their use, certainly renders such use less desirable. Suitable surfactants that are solvent soluble (e.g., hydrophobic) are well known in the art. Preferred examples include polyethoxylated $C_4$ to $C_{18}$ alkyl phenols, polypropoxylated $C_4$ to $C_{18}$ alkyl phenols, $C_8$ to $C_{30}$ alkyl and aralkyl sulfates and sulfonates. The polyamine solvent surfactant mixture comprises at least 0.0005% by weight polyamine, 0.05% by weight surfactant and the balance solvent. In preferred embodiments, there is included 1 to 10% by weight polyamine, 1 to 20% by weight surfactant and the balance solvent. A preferred formulation is:

% By Weight

8% polyamine
3% polyethoxylated nonylphenol
89% kerosene

Upon metering such a premix into an aqueous injection fluid, a dispersion forms which is persistent and tends not to precipitate.

While not necessary to operation, the premix described above can include water so that a stable emulsion is produced.

Although the means or sequence of addition employed to incorporate the antimicrobial in the injection fluid to form the flooding composition of our invention is not critical to performance, we prefer that sufficient mechanical, e.g. an impeller or air, agitation be employed to insure a uniform admixture. One satisfactory technique is to meter or bleed the antimicrobial into the injection fluid immediately prior to its introduction into the well. Also, another satisfactory technique is to prepare a premix of fluid, viscosity modifying agent, and antimicrobial and add this premix to the water or brine stream just prior to injection. Such a premix includes from 0.0005% to 10% by weight of antimicrobial, the remainder being viscosity modifying agent, and optionally water or brine.

To summarize, the oil recovery process of our invention comprises flooding compositions such as injection, displacement and driving fluids to which the antimicrobials described herein have been added and (a) injecting said flooding medium into an injection well penetrating a subterranean oil-bearing formation and (b) forcing said flooding medium through said formation toward at least one output well in said formation.

Acid addition salts of the polyamines are prepared and isolated, if desired, by precipitation, evaporation of solutions or other usually employed techniques.

Suitable anions for the salts include anions derived from inorganic acids as well as those or organic acids such for example as halide, e.g., chloride, bromide or iodide or sulfate, bisulfate, nitrate, phosphate, acetate, propionate, maleate, succinate, laurate, oleate, palmitate, stearate, ascorbate, gluconate, citrate, carbonate, bicarbonate, benzoate, salicylate, pamoate phthalate, furoate, picolinate, dodecylbenzenesulfonate, laurylethersulfate, nicotinate and the like. Generally, any anion derived from an acid is suitable and satisfactory when the polyamine salt anion $X^-$, e.g., chloride is to be replaced with other anions by well known anion exchange techniques.

A typical illustrative enhanced oil recovery formulation comprises:

% By Weight 0.0005-10% polyamine
3-20% surfactant
5-60% water-containing electrolyte
10-60% hydrocarbon cosurfactant, i.e., isopropyl, amyl or hexyl alcohol, cyclohexanone or acetone to provide a system with $5 \times 10^{-5}$ ohm$^{-1}$cm$^{-1}$ conductivity. Electrolyte preferably comprises 5-60 wt. % based on water of NaCl, $Na_2SO_4$, KCl, $K_2SO_4$, KOH or $CaCl_2$.

Substituted bicycloheptanes which are obtained in the syntheses route described herein may be in exo and endo isomer configurations and generally are mixtures of both. Many factors enter into the actual ratio of isomers formed and these can be temperature, solvents, steric effects, equilibration conditions, nature of substituents and others. However, it appears that the utility of this invention is served without the necessity for strictly controlling the isomer composition. The content of a product mixture may be determined by vapor or liquid phase chromatography, NMR spectral analysis, fractional distillation and other methods. It is also possible to isolate pure isomers by selection of these and other separation techniques well known in the art.

The following specific examples are further illustrative of the preparation of the antimicrobials of our invention, but should not be construed as any limitation on the compound presented in the appended claims.

EXAMPLE 1 a. Preparation of
3-(3,3-dimethylnorborn-2-yl)-propionic Acid

To refluxing acetic anhydride (1050 g., 10 moles), there is added dropwise over six hours a solution of camphene (136 g., 1 mole) and di-tert-butyl peroxide (0.1 mole, 14.6 g.). After complete addition, the mixture is heated at reflux for five hours. The cooled reaction mixture is concentrated under reduced pressure to leave a yellow-orange residual oil; 750 ml. of 2.5N NaOH is added to the residue which is then heated on the steam bath for one hour. The cooled solution is extracted once with ether, made acidic with concentrated HCl, and extracted thoroughly with ether. The dried ($Na_2SO_4$) ether extracts are concentrated under reduced pressure and the residue distilled under vacuum to give a colorless product, b.p. 141° C.-144° C./0.5 mm.

b. Preparation of
1,5-Di-(3,3-dimethylnorborn-2-yl)-3-pentanone 3-(3,3-Dimethylnorborn-2-yl)propionic acid (392 g., 2.0 moles) and iron (hydrogen reduced, 61.5 g., 1.1 moles) is heated for 1.5 hours at 195° C. under a nitrogen atmosphere. After that time, the temperature is increased to 290° C. and maintained at that temperature for 3 hours. The cooled reaction mass was extracted well with ether, filtered through Celite, and the ethereal extracts concentrated under vacuum. The residual oil is distilled under vacuum to leave the product as a liquid, b.p. 172° C.-173° C./0.05-0.1 mm.

c. Preparation of
1-[1,5-Di-(3,3-dimethylnorborn-2-yl)-3-pentyl]-1,5,9-triazanonane Trihydrochloride 1,5-Di-(3,3-dimethylnorborn-2-yl)-3-pentanone (6.04 g., 0.02 mole) and 3,3'-iminobispropylamine (13.1 g., 0.10 mole) in 150 ml. toluene is heated at reflux overnight with a Dean-Stark water separator. The cooled solution is concentrated under reduced pressure. The residue is dissolved in ethanol and hydrogenated with $PtO_2$ at room temperature and 40 psi hydrogen pressure. The platinum catalyst is filtered off and the ethanol removed under vacuum. The residual oil is dissolved in ether and the ether solution washed several times with water to remove the excess 3,3'-iminobispropylamine. The ether extracts are dried over anhydrous sodium sulfate and concentrated under vacuum to leave the polyamine as a colorless oil (8.3 g., 100% yield).

The oil is dissolved in ether and hydrogen chloride gas is bubbled into the solution until no further precipitation occurs. The ether is evaporated under reduced pressure to leave the product as a solid which is digested with hot isopropyl alcohol. The solids are collected by filtration and dried under vacuum at 70° C. to give a colorless product 10.8 g., (97%), m.p. 260° C.-262° C.

In an analogous manner, but substituting an equimolar quantity of 1,3-diamino-2-hydroxypropane for the 3,3'-iminobispropylamine, there is prepared 1-[1,5-di-(3,3-dimethylnorborn-2-yl)-3-pentyl]-1,3-diamino-2-hydroxypropane.

What is claimed is:

1. A premix for incorporation into displacing and driving fluids used for injection into oil-bearing strata during oil production subsequent to primary recovery which comprises at least 0.0005% by weight of 1-[1,5-di-(3,3-dimethylnorborn-2-yl)-3-pentyl]-1,5,9-triazanonane, and acid addition salts thereof, at least .05% by weight of a hydrocarbon solvent soluble surfactant, and a hydrocarbon solvent, fluid at ambient temperature.

2. A premix according to claim 1 where said surfactant is a crude oil sulfonate.

3. A premix according to claim 1 where said surfactant is a polyether derived from the reaction product of a hydroxylated non-heterocyclic aromatic hydrocarbon having from 6 to 14 carbon atoms and at least one hydroxy substituent and a $C_2$ to $C_4$ epoxy compound.

4. A premix according to claim 3 where said surfactant is polyethoxylated phenol.

* * * * *